United States Patent [19]

Gillis

[11] Patent Number: 4,587,969
[45] Date of Patent: May 13, 1986

[54] SUPPORT ASSEMBLY FOR A BLOOD VESSEL OR LIKE ORGAN

[76] Inventor: Rolando Gillis, 10725 Westwood Lake Dr., Miami, Fla. 33165

[21] Appl. No.: 695,791

[22] Filed: Jan. 28, 1985

[51] Int. Cl.$^4$ ............................................. A61B 17/11
[52] U.S. Cl. ............................ 128/334 R; 112/262.1
[58] Field of Search ..................... 128/334 R, 335.5; 623/1; 112/262.1, 169

[56] References Cited

U.S. PATENT DOCUMENTS 4,483,339  11/1984  Gillis ............................... 128/334 R

FOREIGN PATENT DOCUMENTS 2546283  11/1974  Fed. Rep. of Germany ... 128/334 R

*Primary Examiner*—Richard C. Pinkham
*Assistant Examiner*—Gary Jackson
*Attorney, Agent, or Firm*—John Cyril Malloy

[57] ABSTRACT

A support assembly for a blood vessel or like hollow, substantially tubular organ, structured for insertion within the vessel to provide sufficient support of the vessel to allow closing of an opening in the vessel by suture or other recognized medical technique. The assembly includes a roll formed from a length of strand wound upon itself to form windings which collectively define the elongated configuration of the roll. A roller is mounted for movement circumferentially about the outer surface of the roll within the vessel or like organ. The relative dimension and disposition of the roller and roll in engaging, supporting relation to the inner surface of the vessel defines an operative space therebetween and which extends at least along the length of the roller. Such space is sufficient to allow placement and otherwise manipulation of the suture for purposes of closing an opening in the vessel. The operative space is continuously displaced along the opening in the vessel upon the selective movement of the roller relative to the roll until the entire opening in the vessel is closed.

10 Claims, 7 Drawing Figures

U.S. Patent   May 13, 1986   4,587,969
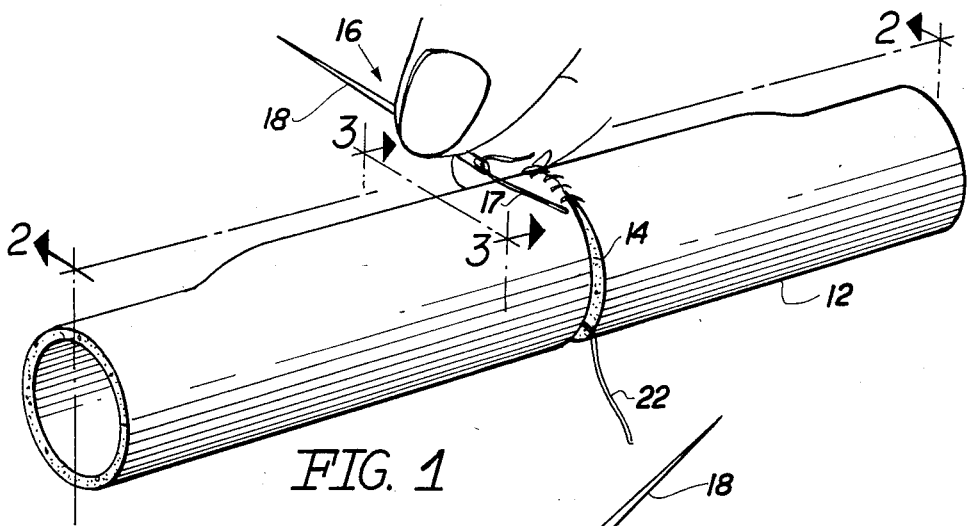
FIG. 1
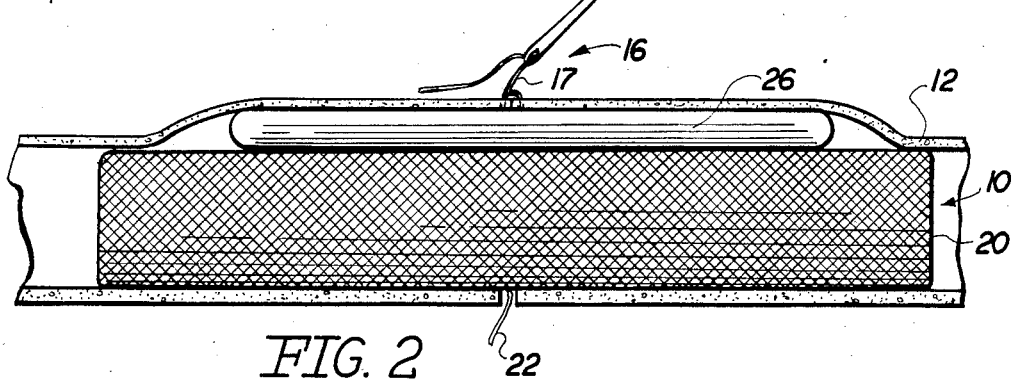
FIG. 2
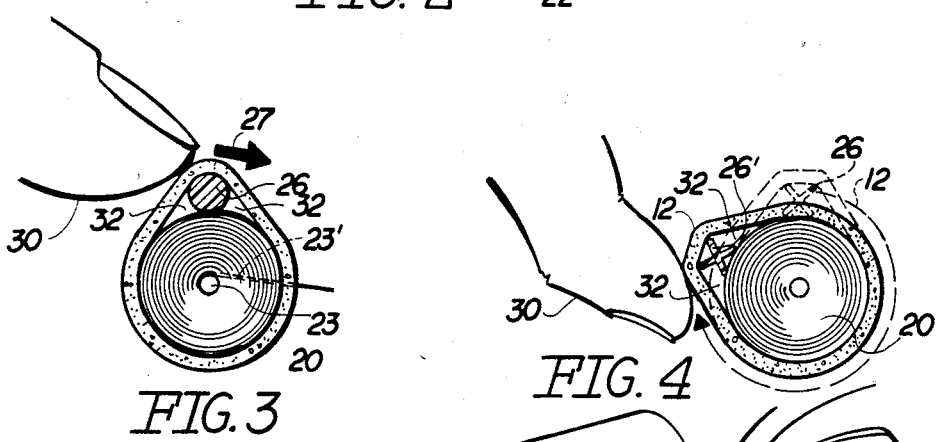
FIG. 3   FIG. 4
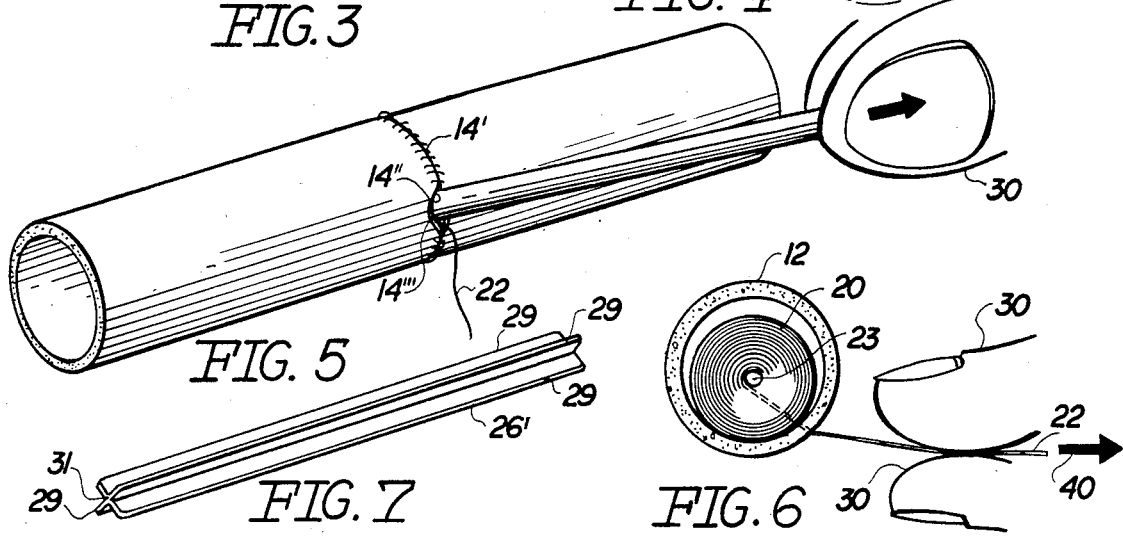
FIG. 5   FIG. 6
FIG. 7

SUPPORT ASSEMBLY FOR A BLOOD VESSEL OR LIKE ORGAN

FIELD OF THE INVENTION

This invention relates to a support assembly designed to be positioned on the interior of a blood vessel or like hollow organ for engagement with the inner surface of the vessel so as to support a portion of the vessel during the closing of an opening such as an incision or the like in the vessel and so as to provide proper support of the vessel for the placement of sutures, staples or the like.

BACKGROUND OF THE INVENTION

In the medical profession a surgeon is frequently required to open a blood vessel, such as a vein or artery, for the purpose of removing plaque or for otherwise repairing the blood vessel due to accident or trauma. The traditional techniques associated with rejoining or closing openings in tubular organs such as blood vessels comprise sewing together the severed periphery of the opening with a very fine thread. It is readily acknowledged that such work is extremely difficult due to its intricacies. It is recognized in the prior art that with precision work of this nature, adequate proper support of the blood vessel during closure thereof is essential is effecting a complete rejoining.

Whether the opening in the vessel is oriented longitudinally of the vessel or substantially transversely such as when the vessel is completely severed, the aforementioned proper support of the vessel is still a requisite to accomplishing proper closure.

The following U.S. patents are related to support and/or manipulation of a tubular organ, such as a blood vessel or the like, when an opening therein is attempted to be closed using substantially conventional surgical techniques. Braun, U.S. Pat. No. 3,562,820; Sparks, U.S. Pat. No. 3,938,524; Ablaza, U.S. Pat. No. 4,190,909; Hardy, U.S. Pat. No. 4,182,339; and Bergentz, U.S. Pat. No. 3,993,078.

All of the above-noted patents are directed not only to the problem of providing proper support but also of removing the support from the interior of the vessel or the like tubular organ once the opening therein is closed or at least partially closed. While the structures and methods disclosed in the above set forth patents are assumed to be operative for their intended function, the present invention is directed to the efficient removal of a support assembly wherein sufficient operative space is provided to accomplish manipulation of the suture or the like so that sewing of the periphery of the opening in the preferred manner can be readily accomplished.

SUMMARY OF THE INVENTION

The present invention relates to a support assembly designed to be placed within a blood vessel or like hollow, tubular organ for support thereof during closing of a surgical opening or other opening formed in the vessel due to accident, trauma, etc. More specifically, the support assemby of the present invention comprises a roll having a somewhat elongated configuration and being dimensioned to fit within the opened blood vessel and supportingly engage a portion of the inner surface of the vessel so that the vessel is supported in the area of the opening therein. The roll is formed from a length of strand wound upon itself to form windings wherein the windings collectively define the overall configuration and dimension of the roll. The single strand from which the windings are formed further includes a pigtail integrally or otherwise secured to the distal extremity thereof. The pigtail is disposed and structured to extend through a portion of the opening of the vessel and exteriorly of the vessel. Removal of the roll from its interior supporting position within the vessel may be accomplished, as set forth hereinafter, by exerting a pulling force on the pigtail such that the windings and the strand from which they are formed will become unravelled continuously.

The supporting assembly of the present invention further includes a roller having an elongated configuration and a longitudinal dimension preferably somewhat less than that of the roll. Similarly, the transverse dimension of the roller is somewhat less than that of the roll. The roller is movably disposed on the outer surface of the roll but dimensioned and disposed to engage the inner surface of the vessel and thereby also be positioned in supporting relation to the vessel in the area of the opening therein.

An operative space is defined between each of two opposite sides of the roller and the roll wherein the roller and the roll are cooperatively structured and dimensioned such that the inner surface of the vessel is disposed out of contact with either the roll or the roller along the length of the operative space. Further, the operative space preferably extends along the length of the roller and is dimensioned so as to provide both adequate support and space for manipulation of the suture, needle, or like instrument used to sew or close the opening formed in the vessel.

An important feature of the present invention is the ability to manipulate the roller so as to move it circumferentially about the outer surface of the roll thereby causing the operative space to also move and be continuously displaced upon movement of the roller in order that access can be obtained to the entire length of the opening formed in the vessel.

In a preferred embodiment of the present invention the roller has a substantially continuous, non-interruptive cylindrical surface along the length thereof. However, in another embodiment of the present invention, the roller comprises a multi-vein configuration or structure including a plurality of individual veins disposed in spaced apart relation to one another and each extending radially outward from a central longitudinal axis of the roller. Regardless of the embodiment, the roller is manipulated so as to be moved circumferentially about the outer surface of the roll and yet be maintained in a substantially parallel orientation thereto so that the length of the roller coincides in a substantially parallel relation with the length of the roll. The formed operative space therefor is positioned on opposite sides of the roller between the roller and the roll and extends parallel to the length of both the roller and the roll.

Another important feature of the present invention is the removal of both the roller and the roll from the interior of the vessel once the opening therein has been almost completely closed. Such removal occurs by manipulating the roller so as to move it longitudinally relative to the vessel in which it is positioned and to the roll on which it moves. This longitudinal sliding of the roller occurs until one end thereof is substantially aligned with a first unopened portion of the opening. This first unopened portion is dimensioned so as to allow slippage or passing of the aligned end of the roller therethrough. Once disposed through the first portion of the opening, it may be grasped by an instrument or by the fingers and pulled through the first portion of the opening until it totally exits the vessel. This first portion, as well as the remainder of the opening is then totally closed with the exception that the aforementioned pigtail extends through this opening to a length which may be easily grasped by the fingers and/or by an instrument. A pulling force is exerted thereon which causes an unravelling of the strand which forms the windings of the roll. The roll effectively becomes unravelled or unwound as the pigtail and strand are pulled from the closed opening or what may be considered a second unopened portion of the opening. Any additional closure of the opening once the pigtail and strand, and therefore the entire roll, has been removed from the interior of the vessel can be accomplished with a minimal amount of effort since the second unopened portion will be of minimum dimension due to the thinness of the strand. In most cases, additional suturing or closing of the opening will not be required once it is found that no leakage occurs through the closed opening.

BRIEF DESCRIPTION OF THE DRAWINGS

For a fuller understanding of the nature of the present invention, reference should be had to the following detailed description taken in connection with the accompanying drawings in which:

FIG. 1 is an isometric view of a blood vessel with opening formed therein wherein the opening is closed utilizing conventional medical techniques and instrumentation.

FIG. 2 is a sectional view along line 2—2 of FIG. 1 showing the interior of the blood vessel and the structure of the subject support asembly as it is positioned within the vessel.

FIG. 3 is a sectional view along line 3—3 of FIG. 1.

FIG. 4 is a sectional view similar to that of FIG. 3 but representing another embodiment of the support assembly and selective positioning of a roller portion relative to a roll portion represented in broken lines.

FIG. 5 is an isometric view showing removal of the roller portion of the subject support assembly.

FIG. 6 is an isometric view showing structural details of the embodiment of FIG. 4 of the roller.

FIG. 7 is a sectional view showing removal of the roll portion of the support assembly of the support assembly.

Like reference numerals refer to like parts throughout the several views of the drawings.

DETAILED DESCRIPTION OF THE PREFERRED EMBODIMENT

As shown in FIGS. 1 and 2, the present invention is directed towards a support assembly generally indicated as 10 designed for positioning within a blood vessel 12 or like hollow, substantially tubular organ wherein an opening 14 is formed in the vessel 12. The subject support assembly 10 is dimensioned, structured and disposed to provide support of the vessel 12 during closing of the opening 14 as when the opening 14 is closed as by suturing or the like utilizing substantially conventional medical instrumentation and technique generally represented as 16. The present invention will be described with reference to closing and opening 14 in vessel 12 as by sewing with a small gauge thread 17 utilizing a closing needle 18. It should be recognized that the support assembly of the present invention is capable of utilization with other instrumentation and technique for closing or repairing vessels 12.

The support assembly 10 comprises a roll having an elongated configuration and formed from a strand wound upon itself to define a plurality of windings. The number and locale of the large number of windings forming the roll are dependent upon its overall dimension and configuration which in turn is dependent upon the size of the vessel 12 or like organ with which the roll 20 is intended for use. Further, and as will be explained in greater detail hereinafter, the strand includes a distal extremity in the form of a pigtail 22 disposed to extend from an inner hollow channel 23 of the roll through an opening therein 23' such that the pigtail or extremity 22 projects outwardly from the outer surface of the roll 20 and further extends through a portion of the opening 14 to a locale exteriorly of the vessel 12.

The support assembly of the present invention further includes a roller 26 being of solid, one-piece construction and having an elongated configuration with a length somewhat less than the length of the roll 20. Similarly, the transverse dimension of roller 26 (see FIGS. 3 and 4) is somewhat less than the transverse dimension of the roll 20. In use, the roller 26 is also disposed on the interior of the vessel 12 wherein both the roll 20 and the roller 26 are disposed in engaging, supporting relation to the interior surface 12' of the vessel 12. Specifically, the combined roller 26 and roll 20 are disposed in direct supporting relation to the vessel 12 in the area at which the opening 14 is located. The roller 26 as well as an additional embodiment 26' of the roller 26 are movable over the outer surface of the roll 20 in a substantially circumferential path of travel. During such movement or repositioning of the roller 26, the roller 26 is maintained in a substantially parallel orientation to the length of the roll 20. Further, such movement or repositioning of the roller 26, in accordance with the directional arrow 27 may occur by manual manipulation of the fingers 30 by the medical personnel involved.

An important feature of the present invention is the creation of an operative space 32 within the interior of the vessel 12 wherein such space extends along opposite sides of the roller 26 and along the length thereof. The operative space 32 is thereby effectively positioned and defined by the spaced apart outer surfaces of roll 20 and roller 26 and is sufficient both in dimension and configuration to allow operative manipulation of the needle 18, or other instrumentation, therein during closing of the opening 14. It can be appreciated that if the opening 14 is disposed substantially transversely to the longitudinal axis of the vessel 12. The roller 26 will pass through a substantially circular path of travel about the circumference of the roll 20. However, if the opening 14 is located longitudinally or somewhat obliquely to the longitudinal axis of the vessel 12, movement of the roller 26 may be somewhat less in distance but the roller will still travel in a substantially circumferential path of travel about the roll 20.

Another embodiment of the present invention is best shown in FIGS. 4 and 7 wherein the roller 26' differs from the structure and configuration of the roller 26. With reference to FIGS. 2 and 3, it is clearly shown that the roller 26 has an outer surface which is substantially continuous and cylindrical. However, the roller 26' has a multi-vein construction and/or configuration wherein a plurality of individual veins 29 are disposed in spaced apart relation to one another and each extend outwardly from a longitudinal center or central axis 31 of the roller 26' (FIG. 7). When the roller 26' is utilized, the operative space 32 is still formed on opposite sides of the roller 26' wherein such space still is dimensioned and configured to allow passage and otherwise manipulation of the needle 15, or like instrumention, in order to facilitate closing of the opening 14.

Once the opening 14 is closed as shown and represented as 14' in FIG. 5, removal of the support assembly 10 is accomplished without derogatorily affecting the closed portion 14' of the opening. Such is accomplished by first longitudinally sliding the roller 26 or 26' along its own length and the length of the roll 20 until one end thereof is disposed in substantial alignment with a first unclosed portion 14' of the otherwise closed opening 14'. Such first portion 14" is sufficiently dimensioned to allow one end, and the entire length, of the roller 26 to pass therethrough so as to allow exiting of the entire roller 26 from the interior of the vessel 12. Once this is accomplished, the first portion 14" can be closed to the extent that the pigtail or distal extremity 22 of the strand from which roll 20 is formed still penetrates exteriorly of the vessel 12. Accordingly, the pigtail 22 extends outwardly from the interior of vessel 12 through a second unopened portion 14'''. Exertion of a pulling force on the pigtail 22 as indicated by directional arrow 40 will cause the roll 20 to become unwound due to a disconnection of the windings from the roll and a general unravelling of the roll. It should be obvious therefor that continued pulling force exerted on the strand and initially on pigtail 22 causes a total unravelling of the roll 20 and its removal through the second unopened portion 14'''. Additional closure of the unopened portion 14''' may be required to stop any leakage or alternately, the second unopened portion 14'''' may be of such a minimal dimension that additional closure steps may not be required to prevent leakage therefrom.

It is therefore to be understood that the following claims are intended to cover all of the generic and specific features of the invention herein described and all of the statements of the scope of the invention which, as a matter of language, might be said to fall therebetween.

Now that the invention has been described, what is claimed is:

1. A support assembly for a blood vessel or like hollow, tubular organ having an opening therein and primarily designed for placement within the vessel during closing of the opening, said assembly comprising:
   (a) a roll formed from a length of strand wound upon itself to form windings, said windings collectively defining the configuration of said roll,
   (b) said roll dimensioned and configured to define an outer surface disposable in supporting engagement with an inner surface of the vessel,
   (c) a pigtail defined by a distal extremity of said length of strand and disposed to extend outwardly from said roll through the vessel and exteriorly thereof,
   (d) a roller having an elongated configuration disposable on the interior of the vessel between said outer surface of said roll and an inner surface of the vessel,
   (e) said roller movable along said outer surface in a substantially circular path of travel about the outer circumference of said roll and movably disposed along said path of travel in continuous, supporting relation to the inner surface of the vessel,
   (f) said roll and said roller relatively dimensioned and disposed to define an operative space therebetween, said operative space movable along with said roll, circumferentially about said roll and in contiguous, communicating relation to the opening in the vessel, whereby the opening in the vessel is closed through utilization of said space and support of peripheral portion of the opening by said roll and roller;
   (g) said roller longitudinally slidable through a first unclosed portion of the opening and said roll passable through a second unclosed portion of the opening upon becoming unrolled upon application of pulling tension to the pigtail,
   (h) whereby both said roll and said roller are independently removable from the vessel subsequent to closure of all but the first and the second unclosed portions of the opening.

2. An assembly as in claim 1 wherein said roller comprises a longitudinal and a transverse dimension less than corresponding dimensions of said roll, said operative space extending longitudinally and in parallel relation to said roller and between said roller and said roll.

3. An assembly as in claim 2 wherein said operative space extends along the length of said roller on opposite sides thereof and between said roll and both of said opposite sides.

4. An assembly as in claim 1 wherein said operative space extends along the length of said roller between said roll and each of two opposite sides of said roller.

5. An assembly as in claim 1 wherein said roller is of a substantially solid one-piece construction including a substantially closed, continuous outer surface formed along the length thereof.

6. An assembly as in claim 5 wherein said roller comprises a transverse dimension less than that of said roll.

7. An assembly as in claim 6 wherein said roller includes a longitudinal dimension less than that of said roll.

8. An assembly as in claim 1 wherein said roller comprises a multi-vein construction defined by a plurality of veins each disposed in spaced relation to one another and extending radially outward from a center thereof, said plurality of vanes extending continuously along the length of said roller.

9. An assembly as in claim 8 wherein said operative space is disposed along the length of said roller between each of two opposite sides of said roller and said roll, said operative space at least partially defined between spaced apart vanes extending along and defining each of said opposite sides.

10. An assembly as in claim 1 wherein said roll further comprises a first end and a second end each integrally formed at respective opposite ends of said outer surface, a centrally disposed channel extending coaxially through said roll and along the length thereof between said first and said second ends, said channel disposed and structured to allow blood flow therethrough and defining a substantially cylindrical inner surface spaced inwardly a predetermined degree from said outer surface along at least a major portion of the length thereof, said windings successively extending from said outer surface to said inner surface to define a continuous cylindrical wall having a thickness equal to said predetermined distance between said outer surface and said inner surface, said predetermined distance dimensioned to be determinative of the amount of support presented to the vessel; said pigtail disposed to extend from said inner surface through an aperture means formed in said wall outwardly therefrom a sufficient distance to protrude through an unclosed portion of the opening in the vessel.

* * * * *